(12) United States Patent
Spinelli et al.

(10) Patent No.: US 8,498,703 B2
(45) Date of Patent: Jul. 30, 2013

(54) METHOD AND SYSTEM FOR TREATMENT OF NEUROCARDIOGENIC SYNCOPE

(75) Inventors: Julio C. Spinelli, Bradenton, FL (US); Qingsheng Zhu, Wexford, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/235,599

(22) Filed: Sep. 19, 2011

(65) Prior Publication Data

US 2012/0010678 A1  Jan. 12, 2012

Related U.S. Application Data

(63) Continuation of application No. 10/862,831, filed on Jun. 7, 2004, now Pat. No. 8,024,040, which is a continuation of application No. 09/917,259, filed on Jul. 27, 2001, now Pat. No. 6,748,271.

(51) Int. Cl.
*A61N 1/16* (2006.01)

(52) U.S. Cl.
USPC ................................. 607/9; 607/17

(58) Field of Classification Search
USPC ............................. 607/4–5, 9, 23, 17–18, 238
See application file for complete search history.

(56) References Cited

U.S. PATENT DOCUMENTS

| | | | |
|---|---|---|---|
| 3,608,542 A | 9/1971 | Pacela et al. | |
| 4,003,379 A | 1/1977 | Ellinwood, Jr. | |
| 4,271,192 A | 6/1981 | Wurtman et al. | |
| 4,470,987 A | 9/1984 | Wurtman et al. | |
| 4,651,716 A | 3/1987 | Forester et al. | |
| 5,213,098 A | 5/1993 | Bennett et al. | |
| 5,441,525 A | 8/1995 | Shelton et al. | |
| 5,464,434 A | 11/1995 | Alt | |
| 5,501,701 A | 3/1996 | Markowitz et al. | |
| 5,540,728 A | 7/1996 | Shelton et al. | |
| 5,676,686 A | 10/1997 | Jensen et al. | |
| 5,706,829 A | 1/1998 | Kadri | |
| 5,725,561 A | 3/1998 | Stroebel et al. | |
| 5,725,562 A | 3/1998 | Sheldon | |
| 5,749,900 A | 5/1998 | Schroeppel et al. | |
| 5,800,464 A * | 9/1998 | Kieval ............................... 607/9 |
| 5,865,760 A | 2/1999 | Lidman et al. | |
| 5,874,420 A | 2/1999 | Pelleg | |
| 5,876,353 A | 3/1999 | Riff | |
| 5,913,879 A | 6/1999 | Ferek-Petric et al. | |

(Continued)

FOREIGN PATENT DOCUMENTS

| | | |
|---|---|---|
| WO | WO 02/053026 | 7/2002 |
| WO | WO 02/053228 | 7/2002 |
| WO | WO 03/020364 | 3/2003 |

OTHER PUBLICATIONS

Response Dated Nov. 5, 2008 to Official Action of Aug. 5, 2008 From the US Patent and Trademark Office Re.: U.S. Appl. No. 10/862,831.

(Continued)

*Primary Examiner* — Rex R Holmes

(57) ABSTRACT

A method and apparatus for treating or preventing neurocardiogenic syncope is disclosed. Upon detection of bradycardia or a drop in blood pressure indicating the onset of syncope, electrostimulation pulses are delivered during the heart's refractory period. The pulses are non-excitatory but increase myocardial contractility and thereby increase cardiac output.

28 Claims, 2 Drawing Sheets

U.S. PATENT DOCUMENTS

| | | | |
|---|---|---|---|
| 5,919,210 | A | 7/1999 | Lurie et al. |
| 5,957,861 | A | 9/1999 | Combs et al. |
| 5,957,957 | A | 9/1999 | Sheldon |
| 6,026,324 | A | 2/2000 | Carlson |
| 6,035,233 | A | 3/2000 | Schroeppel et al. |
| 6,044,297 | A | 3/2000 | Sheldon et al. |
| 6,049,735 | A | 4/2000 | Hartley et al. |
| 6,076,015 | A | 6/2000 | Hartley et al. |
| 6,078,834 | A | 6/2000 | Lurie et al. |
| 6,104,949 | A | 8/2000 | Pitts Crick et al. |
| 6,317,631 | B1 | 11/2001 | Ben-Haim et al. |
| 6,438,408 | B1 | 8/2002 | Mulligan et al. |
| 6,625,492 | B2 * | 9/2003 | Florio et al. ............... 607/17 |
| 6,690,971 | B2 | 2/2004 | Schauerte et al. |
| 6,738,667 | B2 | 5/2004 | Deno et al. |
| 6,748,271 | B2 | 6/2004 | Spinelli et al. |
| 6,907,288 | B2 | 6/2005 | Daum |
| 6,912,420 | B2 | 6/2005 | Scheiner et al. |
| 7,191,000 | B2 | 3/2007 | Zhu et al. |
| 7,333,854 | B1 | 2/2008 | Brewer et al. |
| 8,024,040 | B2 | 9/2011 | Spinelli et al. |
| 2002/0115939 | A1 | 8/2002 | Mulligan et al. |
| 2002/0147475 | A1 | 10/2002 | Scheiner et al. |
| 2002/0147476 | A1 | 10/2002 | Daum |
| 2003/0023279 | A1 | 1/2003 | Spinelli et al. |
| 2003/0028221 | A1 | 2/2003 | Zhu et al. |
| 2003/0074029 | A1 | 4/2003 | Deno et al. |
| 2003/0191503 | A1 | 10/2003 | Zhu et al. |
| 2004/0049235 | A1 | 3/2004 | Deno et al. |
| 2005/0021098 | A1 | 1/2005 | Spinelli et al. |

OTHER PUBLICATIONS

2nd Notice of Allowance Dated Jun. 16, 2011 From the US Patent and Trademark Office Re.: U.S. Appl. No. 10/862,831.

Notice of Allowance Dated Dec. 14, 2010 From the US Patent and Trademark Office Re.: U.S. Appl. No. 10/862,831.

Official Action Dated Aug. 5, 2008 From the US Patent and Trademark Office Re. : U.S. Appl. No. 10/862,831.

Official Action Dated Oct. 10, 2007 From the US Patent and Trademark Office Re. : U.S. Appl. No. 10/862,831.

Official Action Dated Mar. 18, 2009 From the US Patent and Trademark Office R e. : U.S. Appl. No. 10/862,831.

Official Action Dated Jun. 24, 2010 From the US Patent and Trademark Office Re.: U.S. Appl. No. 10/862,831.

Official Action Dated Mar. 26, 2007 From the US Patent and Trademark Office Re. : U.S. Appl. No. 10/862,831.

Response Dated May 7, 2008 to Official Action of Feb. 7, 2008 From the US Patent and Trademark Office Re.: U.S. Appl. No. 10/862,831.

Response Dated Sep. 23, 2010 to Official Action of Jun. 24, 2010 From the US Patent and Trademark Office Re.: U.S. Appl. No. 10/862,831.

Berman et al. "Transthoracic Electrical Impedance as a Guide to Intravascular Overload", Archives of Surgery, 10(1): 61-64, Jan. 1971.

Charach et al. "Transthoracic Monitoring of the Impedance of the Right Lung in Patients With Cardiogenic Pulmonary Edema", Critical Care Medicine, 29(6): 1137-1144, Jun. 2001.

Kusumoto et al. "Cardiac Pacing", The New England Journal of Medicine, 334(2): 89-98, Jan. 11, 1996.

Lau et. al. "Rate-Responsive Pacing With a Pacemaker That Detects Respiratory Rate (Biorate): Clinical Advantages and Complications", Clinical Cardiology, 11(5): 318-324, May 1988.

Luepker et al. "Transthoracic Electrical Impedance: Quantitative Evaluation of a Non-Invasive Measure of Thoracic Fluid Volume", American Heart Journal, 85(1): 83-93, Jan. 1973.

Mai et at "Enhanced Rate Response Algorithm for Orthostatic Compensation Pacing", Pacing and Clinical Electrophysiology, PACE, 23(11/Pt.2): 722, Apr. 2002. Abstract.

Nappholz et al. Rate-Adaptive Pacing Based on Impedance-Derived Minute Ventilation, Clinical Cardiac Pacing, Chap.12: 219-233, 1995.

Petersen et al. "Cardiac Pacing for Vasovagal Syncope: A Reasonable Therapeutic Option?", Pacing and Clinical Electrophysiology, PACE, 20(3/Pt.2): 824-826, Mar. 1997. Abstract.

Pomerantz et al. "Transthoracic Electrical Impedance for the Early Detection of Pulmonary Edema", Surgery, 66(1): 260-268, Jul. 1969.

Shoemaker et al. "Multicenter Trial of a New Thoracic Electrical Rioimpedance Device for Cardiac Output Estimation", Critical Care Medicine, 22(12): 1907-1912, Dec. 1994.

Sra et al. "Cardiac Pacing During Neurocardiogenic (Vasovagal) Syncope", Journal of Cardiovascular Electrophysiology, 6(9): 751-760, Sep. 1995. Abstract.

Viirola et al. "Controlled Growth of Antimony-Doped Tin Dioxide Thin Films by Atomic Layer Epitaxy", Thin Solid Films, 251: 127-135, Nov. 1994.

Viirola et al. "Controlled Growth of Tin Dioxide Thin Films by Atomic Layer Epitaxy", Thin Solid Films, 249(2): 144-149, Sep. 1994.

Visokay et al. "Application of HfSiON as a Gate Dielectric Material", Applied Physics Letters, 80(17): 3183-3185, Apr. 29, 2002.

Wucrz et al. "Effects of Prehospital Medications on Mortality and Length of Stay in Congestive Heart Failure", Annals of Emergency Medicine, 21(6): 669-674, Jun. 1992.

Yu et al. "Early Warning of CHF Hospitalization by Intra-Thoracic Impedance Measurement in CHF Patients With Pacemakers", Pacing and Clinical Electrophysiology, PACE, Abstract Session 4, 24: 19, Apr. 2001.

* cited by examiner

METHOD AND SYSTEM FOR TREATMENT OF NEUROCARDIOGENIC SYNCOPE

RELATED APPLICATIONS

This application is a continuation of U.S. patent application Ser. No. 10/862,831 filed on Jun. 7, 2004, now U.S. Pat. No. 8,024,040, which is a continuation of U.S. patent application Ser. No. 09/917,259 filed on Jul. 27, 2001, now U.S. Pat. No. 6,748,271. The contents of all of the above applications are incorporated by reference as if fully set forth herein.

FIELD OF THE INVENTION

This invention pertains to implantable medical devices and to methods for treating syncopal episodes.

BACKGROUND

Syncope, or fainting, is a transient loss of consciousness and postural tone that may be due a number of etiologies, both cardiovascular and non-cardiovascular. The most common pathophysiogical basis of syncope is an acute decrease in cerebral blood flow secondary to a decrease in cardiac output, thereby causing cerebral hypoxia. Such a decrease in cardiac output can be due to, for example, cardiac arrhythmias or cardiac outflow obstructions. Neurocardiogenic syncope is a relatively benign condition in which dysfunction of the autonomic nervous system causes an inappropriate slowing of the heart (bradycardia) to result in hypotension. Classic neurogenic syncope (vasovagal syncope) occurs when inappropriate reflex inhibition of the sympathetic nervous system and increased parasympathetic activity causes both bradycardia and peripheral vasodilation. Vasovagal syncope may occur in otherwise healthy individuals and in patients with a variety of underlying diseases. A number of factors may precipitate vasovagal syncope, including a hot or crowded environment, alcohol, extreme fatigue, hunger, chronic recumbency, prolonged standing, and emotional or stressful situations. Another type of neurocardiogenic syncope involves failure of the baroreceptor reflex to transiently increase the heart rate when an individual rises to an upright position, causing venous pooling in the lower extremities and decreased venous return to the right side of the heart.

Even if the cause of the syncope is benign, however, its consequences may not be. Falls during syncope can result in fractures, and episodes that occur while driving can be extremely dangerous. Chronic and recurring syncope can create a level of functional impairment similar to that produced by other chronic debilitating disorders.

SUMMARY OF THE INVENTION

The present invention is a system and method for preventing and/or treating syncope with cardiac electrostimulation delivered by an implantable medical device that increases cardiac output. The heart rate is monitored and, when bradycardia below a specified limit value is detected that indicates the onset of a syncopal episode, electrostimulation pulses are delivered to a ventricle during its refractory period. Such electrostimulation pulses are non-excitatory but serve to increase the contractility of the ventricle. Stroke volume and cardiac output are thereby increased in order to prevent or lessen the severity of the syncopal episode.

DETAILED DESCRIPTION

The present invention for treating neurocardiogenic syncope may be incorporated into various types of cardiac rhythm management devices having means for sensing and electrostimulating the heart. As will be described below, the invention may most conveniently be incorporated into a pacemaker.

1. System Description

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing. (As the term is used herein, a pacemaker is any cardiac rhythm management device with a pacing functionality, regardless of any other functions it may perform such as the delivery cardioversion or defibrillation shocks to terminate atrial or ventricular fibrillation.)

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
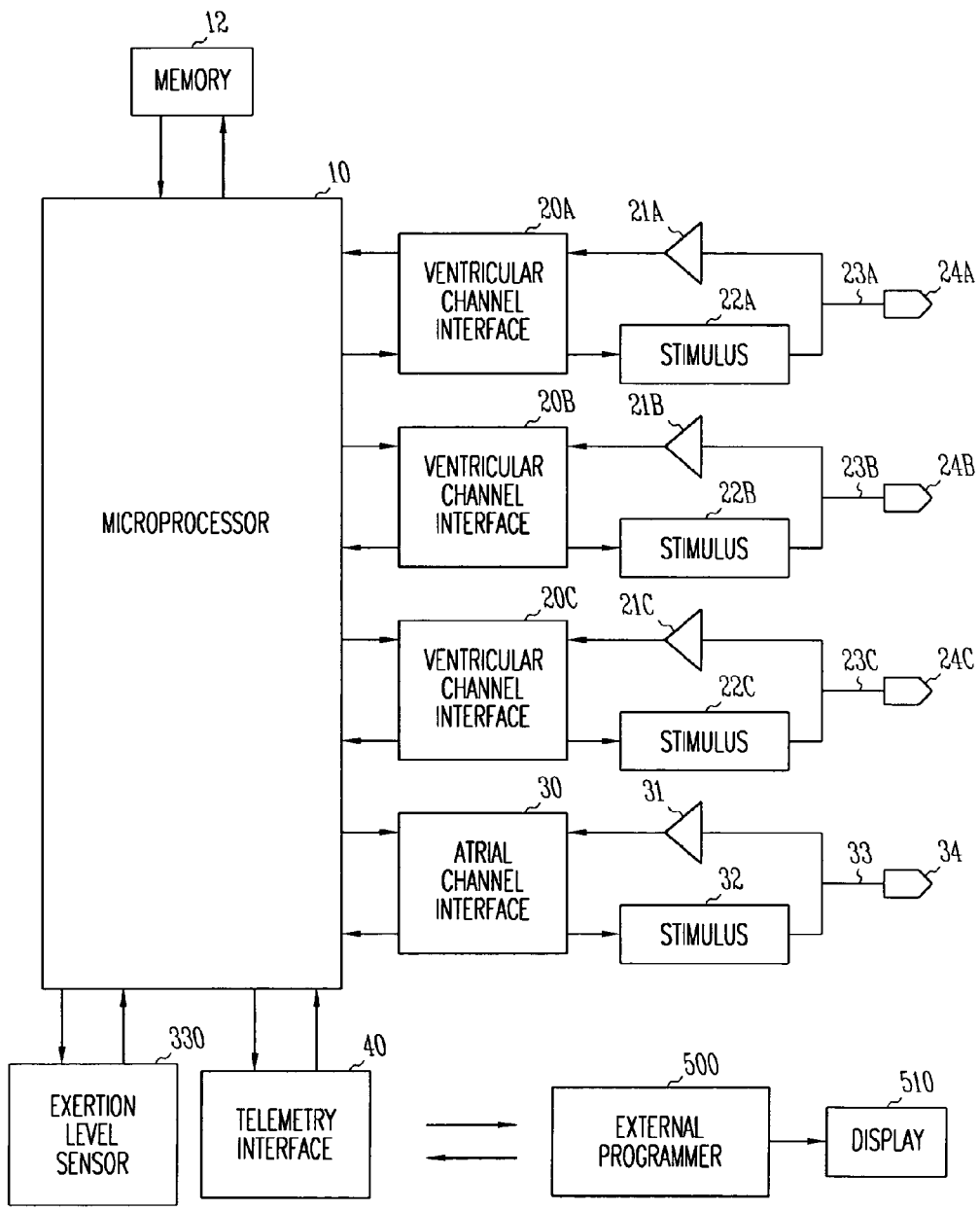
FIG. 1 is a system diagram of an exemplary cardiac rhythm management device.

FIG. 1 shows a system diagram of a microprocessor-based cardiac rhythm management device suitable for delivering various cardiac rhythm management therapies including treatment of neurocardiogenic syncope as detailed below. The device is a pacemaker that is physically configured with sensing and pacing channels for both atria and both ventricles. The controller 10 of the device is a microprocessor that communicates with a memory 12 via a bidirectional data bus. The memory 12 typically comprises a ROM (read-only memory) for program storage and a RAM (random-access to memory) for data storage. The pacemaker has an atrial sensing and pacing channel comprising electrode 34, lead 33, sensing amplifiers 31, pulse generators 32, and atrial channel interface 30 which communicates bidirectionally with microprocessor 10. The device also has a plurality of ventricular sensing and pacing/stimulation channels for one or both ventricles, three of which are shown as comprising electrodes 24a-c, leads 23a-c, sensing amplifiers 21a-c, pulse generators 22a-c, and ventricular channel interfaces 20a-c. In this embodiment, a single electrode is used for sensing and pacing in each channel, known as a unipolar lead. Other embodiments may employ bipolar leads that include two electrodes for outputting a pacing pulse and/or sensing intrinsic activity. The channel interfaces 20a-c and 30 may include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 that has an associated display 510.

Bradycardia pacing modes refer to pacing algorithms used to pace the atria and/or ventricles when the intrinsic ventricular rate is inadequate either due to AV conduction blocks or sinus node dysfunction. Such modes may either be single-chamber pacing, where either an atrium or a ventricle is paced, or dual-chamber pacing in which both an atrium and a ventricle are paced. Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

2. Cardiac Contractility Modulation

In accordance with the invention, when bradycardia below a specified threshold that could otherwise cause syncope is detected by the device, one or more electrostimulatory pulses are delivered to the heart during the refractory period of one or more heartbeats. Such stimulation, referred to herein as cardiac contractility modulation (CCM), is non-excitatory because it is delivered during the refractory period of the ventricle. (The refractory period of the ventricle in this case refers to that portion of the ventricle to which is delivered the electrostimulatory pulse being refractory.) It has been found that such stimulation causes an increase in myocardial contractility, presumably by increasing intracellular calcium concentration. The increase in contractility increases stroke volume so that more blood is pumped in a subsequent systolic contraction. The increased stroke volume counteracts the bradycardia and thereby stabilizes cardiac output to either prevent or shorten the duration of a syncopal episode. The invention may be a dedicated implantable device or incorporated into an implantable cardiac rhythm management device such as a pacemaker, implantable cardioverter/defibrillator, or combination device.

Figure 2:
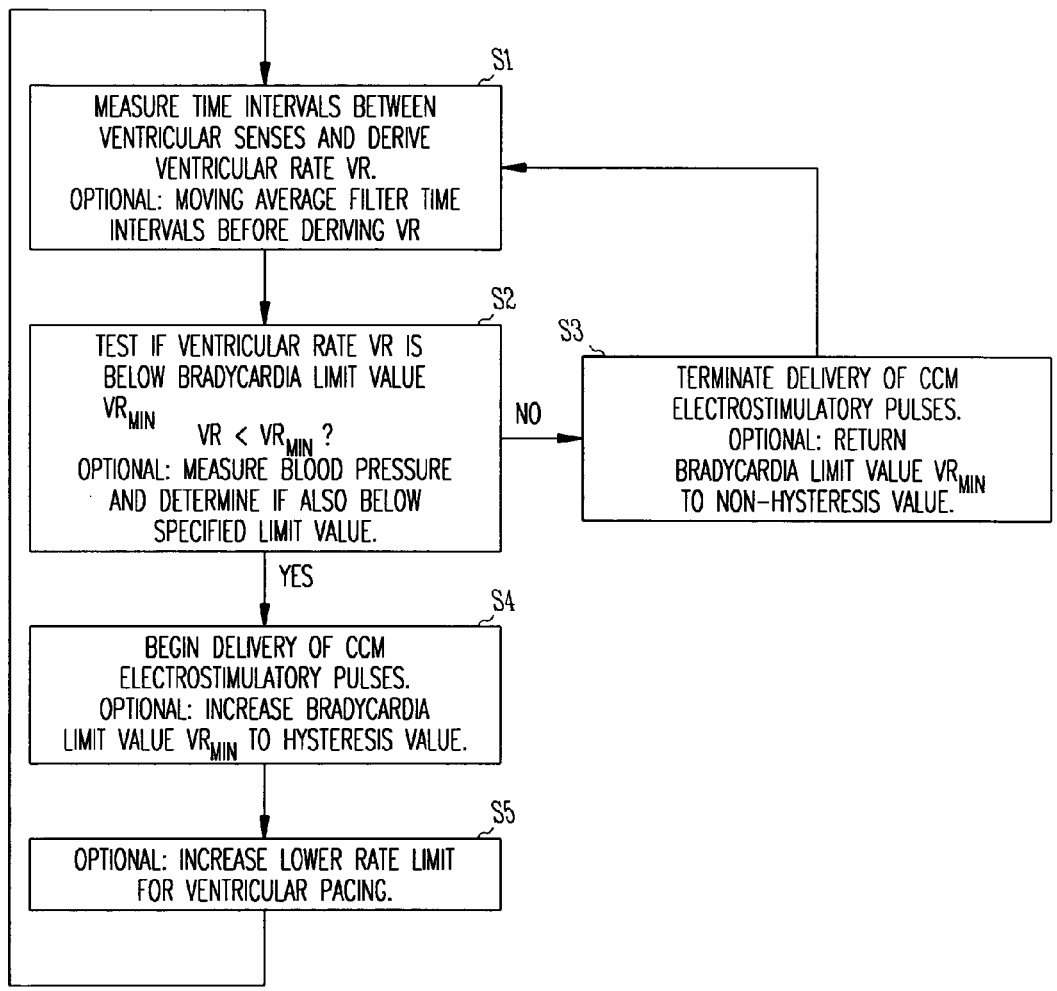
FIG. 2 is a flowchart illustrating an exemplary control scheme for implementing the invention.

Sensing of cardiac activity and delivery of CCM stimulatory pulses may be accomplished using sensing/pacing channels otherwise used for pacing the ventricles with a bradycardia pacing mode or using channels dedicated for the purpose of delivering CCM pulses. In the device shown in FIG. 1, for example, any of the ventricular sensing/pacing channels may be used for delivering CCM stimulation pulses. FIG. 2 illustrates a basic control scheme for carrying out the method as would be implemented by programming the microprocessor 10. In the illustrated scheme, several optional steps are described that may or may not be implemented in various embodiments. At step S1, the ventricular rate is continuously monitored by receiving ventricular senses representing intrinsic ventricular depolarizations from one of the ventricular sensing channels. To derive the ventricular rate VR, the interval between successive ventricular senses is measured and compared to a maximum limit value in order to detect bradycardia as shown at step S2, where the inverse of the interval corresponding to the ventricular rate VR is compared with a bradycardia limit value $VR_{min}$. Bradycardia is detected if $VR<VR_{min}$, and delivery of CCM stimulation pulses is then initiated at step S4 using one of the ventricular stimulation channels. The stimulation pulses are delivered during the refractory period of the ventricle by timing a pulse to occur within a refractory interval following a ventricular sense or a ventricular pace if the device is also operating in a bradycardia pacing mode. The device then returns to the monitoring of the ventricular rate at step S1, and delivery of CCM pulses is terminated at step S3 if the ventricular rate VR equals or exceeds the limit value $VR_{min}$. Optionally, the limit value $VR_{min}$ may be increased to a hysteresis value $VR_{min}$ at step S4 so that CCM pulse delivery is maintained until the heart rate rises above an increased bradycardia limit value. In that case, the bradycardia limit value is returned to a non-hysteresis value at step S3 when CCM pulse delivery is terminated. In another option, if the device is also operating in a bradycardia pacing mode, the lower rate limit may be increased upon detection of bradycardia as shown at step S5. The heart is then paced at a faster rate simultaneously with the application of cardiac contractility modulation.

Modifications may be made to the method so that one or more additional criteria are employed to confirm that a syncopal episode is taking place before CCM stimulatory pulses are delivered. One such modification is shown at step Si where the measured intervals between ventricular senses are moving average filtered in order to derive the ventricular rate VR. The moving average filter smooths the ventricular rate so that bradycardia is not detected when long intervals occur solely due to the variability of the instantaneous rate. Another optional modification is to measure the blood pressure as shown at step S2 and deliver CCM stimulatory pulses only if it is below a specified limit value. The blood pressure measurement may be used instead of a sensed heart rate decrease or may be used to confirm the rate decrease before initiating therapy. One way of measuring blood pressure in a cardiac rhythm management device is to use an accelerometer, such as the exertion level sensor 330, as described in U.S. Pat. No. 6,026,324, issued to Carlson and hereby incorporated by reference. In a further refinement, the magnitude and/or duration of the CCM pulses can be increased as the measured blood pressure decreases in order to maximize the effectiveness of the therapy.

Cardiac contractility modulation may also be applied to multiple sites in order to distribute the effects of the stimulation pulses. Because this type of non-excitatory stimulation also increases local oxygen consumption, distributing the stimulation over a plurality of sites serves to help prevent potentially deleterious effects at the stimulation sites. Accordingly, at step S5 the ventricular stimulation channels can be alternated with each stimulatory pulse so that the pulses are alternately delivered to electrodes 24a-c.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac stimulator, comprising:
   (a) monitoring a heart rate;
   (b) detecting an indication of the onset of a syncopal episode, based on said monitoring;
   (c) in response to said detecting, initiating delivery of one or more electro-stimulation pulses to a heart, timed to be delivered during a refractory period of the site to which they are applied, in a manner which at least partly alleviates or avoids syncope, wherein said delivery includes the delivery of nonexcitatory electric energy to the heart for the purpose of cardiac contractility modulation;
   (d) repeating said detecting;
   (e) repeating said initiating based on said repeated detection; and
   (f) terminating delivery of said pulses after said detecting indicates no syncopal episode.

2. A method according to claim 1, wherein the method further comprises pacing said heart and wherein said delivery is not done on beats that are paced.

3. A method according to claim 1, comprising increasing a cardiac output of said heart by said one or more electro-stimulation pulses.

4. A method according to claim 1, wherein the method further comprises pacing said heart and wherein a same channel is used for pacing and for said delivery.

5. A method according to claim 1, wherein said delivery comprises delivery to multiple sites in the heart.

6. A method according to claim 1, wherein said detecting comprises detecting a reduction in blood pressure.

7. A method according to claim 1, wherein said detecting comprises detecting a reduction in heart rate.

8. A method according to claim 1, comprising pacing said heart to increase a ventricular contraction rate thereof.

9. A method according to claim 1, comprising applying a hysteresis factor to modify detection of syncope while said electro-stimulation is being delivered.

10. A method according to claim 1, comprising modifying one or both of an intensity and duration of said delivery in response to a measured blood pressure.

11. A method according to claim 10, comprising measuring said blood pressure using an accelerometer.

12. A method according to claim 1, wherein said timed delivery comprises delivering said one or more pulses following and timed to the application of a pacing pulse.

13. A method according to claim 1, wherein said timed delivery comprises delivering said one or more pulses following and timed to a ventricular sense.

14. A cardiac stimulator comprising:
   (a) one or more sensing channels configured to monitor a heart rate and to detect an indication of the onset of a syncopal episode, based on the monitoring;
   (b) a stimulation channel adapted to deliver one or more electro-stimulation pulses suitable to increase cardiac contractility when delivered during a refractory period of cardiac tissue to which they are delivered; and
   (c) a controller configured to
      (i) determine one or both of bradycardia and syncope based on input from said sensing channel;
      (ii) initiate delivery of said one or more pulses on said channel, based on said determination, at a timing which is during a refractory period for sites to which pulses are delivered, wherein said delivery includes the delivery of non-excitatory electric energy to the heart for the purpose of cardiac contractility modulation; and
      (iii) terminate delivery of said one or more pulses based on a determination of no bradycardia or no syncope.

15. A stimulator according to claim 14, integrated into a pacemaker.

16. A stimulator according to claim 14, formed as a stand-alone device.

17. A stimulator according to claim 14, wherein said stimulation channel is shared by pacing and non-pacing signals.

18. A stimulator according to claim 14, wherein said sensing channel is shared by pacing logic and logic for delivery of non-excitatory signals of said controller.

19. A stimulator according to claim 14, comprising electrodes connected to multiple delivery sites in the heart.

20. A Stimulator according to claim 14, wherein said controller is configured to modify one or both of an intensity and duration of said delivery in response to a measured blood pressure.

21. A Stimulator according to claim 14, wherein said controller is configured to calculate a timing based on an incoming sensing.

22. A Stimulator according to claim 14, wherein said controller is configured to calculate a timing based on the timing of an outgoing pacing signal.

23. A Stimulator according to claim 14, wherein said controller is configured to determine one or both of bradycardia and syncope based on comparing input from said sensing channel with a bradycardia or syncope specified threshold.

24. A Stimulator according to claim 14, wherein said controller is configured to initiate delivery of said one or more pulses on said channel only based on said determination.

25. A method according to claim 1, wherein initiating delivery of one or more electro-stimulation pulses to a heart is only in response to said detecting.

26. A method according to claim 1, wherein said delivery causes an increase in intracellular calcium concentration.

27. A method according to claim 1, wherein detecting an indication of the onset of a syncopal episode comprises detecting a drop in (LV) blood pressure.

28. A stimulator according to claim 14, wherein said one or more sensing channels are configured to detect a drop in (LV) blood pressure, and wherein said controller is configured to determine syncope based on said detection of drop in (LV) blood pressure.

* * * * *